United States Patent [19]

Spooner

[11] Patent Number: 5,344,406
[45] Date of Patent: Sep. 6, 1994

[54] METHOD AND APPARATUS FOR PROTECTIVELY STABILIZING AND SECURING AN INTRAVENOUS DEVICE

[76] Inventor: James J. Spooner, 16203 E. Glendora Dr., Fountain Hills, Ariz. 85268-3108

[21] Appl. No.: 135,908
[22] Filed: Oct. 13, 1993
[51] Int. Cl.$^5$ .............................................. A61M 5/32
[52] U.S. Cl. ...................... 604/179; 128/879; 128/DIG. 26
[58] Field of Search ............... 128/878, 879, DIG. 26; 604/179, 174, 180

[56] References Cited

U.S. PATENT DOCUMENTS

| | | | |
|---|---|---|---|
| 973,330 | 10/1910 | Wood | 128/879 |
| 2,043,153 | 6/1936 | Cox | 128/879 |
| 3,084,686 | 4/1963 | Perconti | 128/879 |
| 3,561,441 | 2/1971 | Lombardi | 128/156 |
| 3,747,374 | 7/1973 | Meyer | 66/195 |
| 4,470,410 | 9/1984 | Elliott | 128/DIG. 26 |
| 4,591,356 | 5/1986 | Christie | 604/179 |
| 4,905,692 | 3/1990 | More | 606/151 |
| 4,973,314 | 11/1990 | Garrett | 128/DIG. 26 |
| 5,016,648 | 8/1991 | Brown et al. | 128/879 |
| 5,019,050 | 5/1991 | Lynn et al. | 604/179 |
| 5,084,026 | 1/1992 | Shapiro | 604/179 |
| 5,188,608 | 2/1993 | Fritts | 604/179 |

*Primary Examiner*—Paul J. Hirsch
*Attorney, Agent, or Firm*—Donald J. Lisa; Steven Lin

[57] ABSTRACT

A method and apparatus for protectively stabilizing and securing a intravenous device to a patient's body member. The method and apparatus comprise the use of a tubular sleeve made of stretchable fabric having two open ends. The intravenous device is attached to a patient's particular body member. The sleeve is stretched to encircle and elastically retain to the body member, and the sleeve has a plurality of spacings for ventilating the body member. The intravenous device is thereby secured between the sleeve fabric and the body member. The stretchable fabric is an elastic, soft, resilient material through which the body member is easily insertable while allowing the body member to easily and fully move therein.

11 Claims, 1 Drawing Sheet

METHOD AND APPARATUS FOR PROTECTIVELY STABILIZING AND SECURING AN INTRAVENOUS DEVICE

BACKGROUND OF THE INVENTION

1. Fields of the Invention

The present invention relates generally to stabilizing and securing an intravenous device to a patient's body member, and more particularly, to a method and apparatus for securing and stabilizing an intravenous device that uses a tubular sleeve made of a stretchable fabric that has two open ends and a plurality of spacings for ventilating the body member. The stretchable fabric is made from an elastic, soft, resilient material to allow the body member to be easily insertable into the sleeve and to further allow the body member to fully and easily move therein. The intravenous device is thereby secured between the sleeve fabric and the body member.

2. Discussion of Background and Prior Art

Intravenous devices are widely used in the medical field for injecting various type liquids such as medications, vitamins, nutrients, and blood into a patient's body. An intravenous device typically uses a container for holding the liquid, a needle or catheter for injecting the intravenous liquid into the patient's body, and a tube that connects the needle or catheter to the container. The needle is injected into a peripheral vein of a particular body member of the patient, such as a hand, arm, foot or leg, and the liquid flows from the container, through the tube, and into the patient's vein where the needle is injected. The needle and connecting tube, therefore, need to be secured to the body member. Furthermore, they must be secured in a way to prevent the intravenous device from being accidentally dislodged or removed from the patient's vein and to also protect the patient from being injured in any other way by the intravenous needle.

Adhesive tape has often been used to secure an intravenous device to a patient's body member. The problem with adhesive tape, however, is that the tape does not hold the intravenous device very well when the patient moves his body member, and the intravenous needle may continuously dislodge from the patient's skin or vein. The adhesive portion of the tape also wears over time, and the tape must be periodically replaced. Furthermore, adhesive tape is uncomfortable to the patient when it is adhered to his skin particularly when it is removed, usually pulling body hair out with it. Also, tape is usually not very flexible for allowing the body member that is taped to be able to fully and easily move therein. Adhesive tape also does not provide very much ventilation to the patient's body member, and this lack of ventilation causes further discomforts to the patient.

Arm bands have also been used to secure an intravenous device to a patient's body member. An arm band typically includes a strip of durable flexible material and a means for attaching the needle to the band (i.e. a hole in the strip or latches on the strip to which the needle is attached). The arm band is usually wrapped around the arm and secured by securing means, such as VELCRO strips. The arm band can also be adapted to secure around other body members, such as a patient's leg. The needle is then inserted into the patient's vein and is attached to the arm band at or near the attaching means. The main problems with these bands are that they are normally not very comfortable for the patient to wear, and they also do not provide much ventilation to the patient's body member.

Glove type intravenous device holders also exist and have been used. The glove typically includes various means for inserting a patient's hands through the glove and a means for attaching the needle to the glove (i.e. a hole in the glove or a lengthwise slit in the back side of the glove). The glove is inserted and fitted onto the patient's hand through the patient's fingers. A glove having a slit in its back side may be secured by a securing means, such as VELCRO strips, attached along the inner flaps near the lengthwise slit. The securing means ensures that the glove fits snugly to the hand. The needle is inserted into the patient's vein and the glove secures the intravenous device to the patient's hand. The problem with these gloves is that because of their snug fit, they do not provide much ventilation to the patient's hand. At times, a patient's hand does not insert very easily into a glove because of the size differences between the glove and hand. A glove can be cumbersome and not very comfortable for a patient to wear. A further problem with a glove is that it is limited to use on a patient's hand, and cannot be adapted for use on any other patient body part.

Straps also have been employed for securing an intravenous device to a patient's body member. An intravenous needle is inserted into the patient's vein at a particular body member, and an adhesive part of the strap is placed over the needle. The strap is then wrapped around the body member and parts of the tube so that the needle and tube are secured to the body member. One problem with these straps is that they require the use of adhesive, which results in the problems that were discussed earlier (i.e. uncomfortable and wears out over time). Other problems with using a strap is that it may be uncomfortable for a patient to wear, and it may also leave marks on the patient's skin when the strap is removed. A strap is also not very easily mounted to hold the intravenous device since it has to be wrapped several times around the patient's body member.

A device that is in the prior art which can be adapted to be used for stabilizing and securing an intravenous apparatus is an elastic tubular sleeve. The prior art sleeve is typically used as a body cover on injured areas such as broken bone areas, wounds, and the like. The body member that needs treatment is inserted into the sleeve, and the cast or bandage is placed over the sleeve. The sleeve prevents the cast or bandage from sticking to the injured body member allowing these items to be replaced more easily. Presently, however, such prior elastic tubular sleeve have not been adapted or used for stabilizing or securing an intravenous apparatus to a patient's body member.

In overcoming the problems and limitations of the prior art, it is an object of the present invention to protectively stabilize and secure an intravenous device to a patient's body member using a tubular sleeve made of a stretchable fabric that encircles the body member and is elastically retained thereon.

It is another object of the present invention to provide a tubular sleeve made of a stretchable fabric that ventilates the body member to which the intravenous device is stabilized and secured.

It is a further object of the present invention to provide a tubular sleeve for stabilizing and securing an intravenous device made of a stretchable, elastic, soft, resilient fabric material so that the patient's body member is easily inserted into the sleeve and is able to fully and easily move therein.

It is still a further object of the present invention to adapt an elastic tubular sleeve to protectively stabilize and secure an intravenous device to a patient's body member.

SUMMARY OF THE INVENTION

Set forth below is a brief summary of the invention in order to solve the foregoing problems and achieve the foregoing and other objects, benefits, and advantages in accordance with the purposes of the present invention as embodied and broadly described herein.

One aspect of the invention is a method for protectively stabilizing and securing an intravenous device to a patient's body member involving the steps of providing a tubular sleeve made of stretchable fabric having two open ends and a plurality of tiny spacings for ventilating the body member, attaching the intravenous device to the body member, inserting a body member through the sleeve so that the sleeve encircles and is elastically retained on the body member, enlarging the spacings in the sleeve when the sleeve is encircled over the body members, and securing the intravenous device between the sleeve fabric and the body member.

A second aspect of the invention is to provide an apparatus for protectively stabilizing and securing an intravenous device to a patient's body member in which the apparatus is soft, flexible, very comfortable, and easy to wear by the patient for long periods of time. The patient's body member is also movable within the apparatus, and the body member is ventilated for additional comfort to the patient.

DETAILED DESCRIPTION OF THE INVENTION

Figure 1:
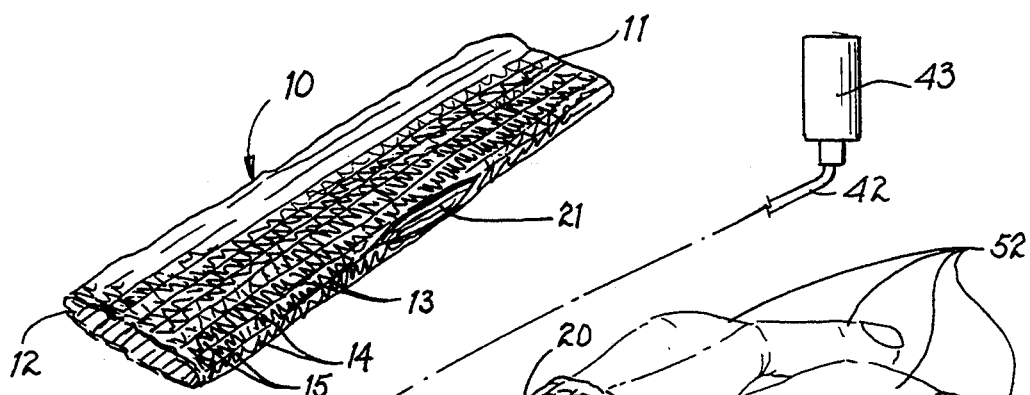
FIG. 1—Perspective view of the tubular fabric sleeve material.
Figure 2:
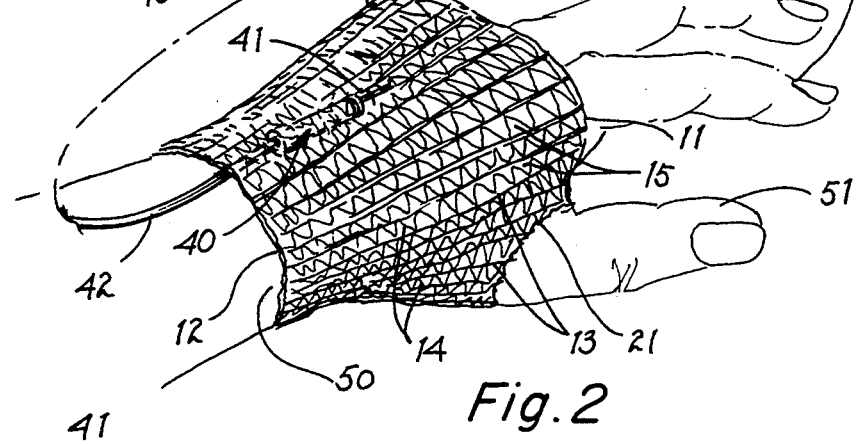
FIG. 2—Perspective view of a first embodiment of a tubular sleeve stabilizing and securing an intravenous device to the back side of a patient's hand.
Figure 2A:
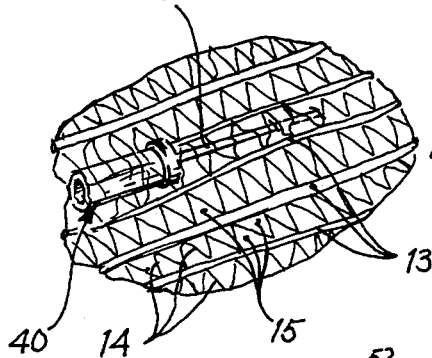
FIG. 2A—Enlarged view of FIG. 2 showing the fabric pattern of the tubular sleeve and the intravenous device stabilized and secured to a patient's hand.
Figure 3:
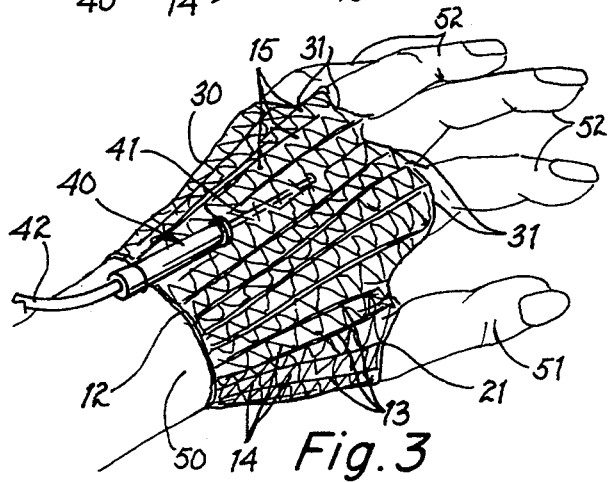
FIG. 3—Perspective view of a second embodiment of a tubular sleeve stabilizing and securing an intravenous device to the backside of a patient's hand.

FIG. 1 shows the tubular, fabric, sleeve material 10, and FIGS. 2A and 3 respectively show a first embodiment 20 and a second embodiment 30 of the present invention for protectively stabilizing and securing an intravenous device. The sleeve material 10 and the two sleeves 20 and 30 are now described in more detail.

The Sleeve Material

FIG. 1 shows sleeve material 10 which is used for making sleeves 20 and 30 in FIGS. 2 and 3 for stabilizing and securing an intravenous device. The sleeve material 10 is a stretchable, tubular, fabric material made from stretchable, resilient yarn filaments 13 and 14. The sleeve material 10 is cut or manufactured to a certain length depending on the size of the body member that is to be inserted into the sleeve, and material 10 has a first open end 11 and a second open end 12.

Yarn filaments 13 are located vertically along the material 10, and yarn filaments 14 are knitted between each yarn filament 13 so that all yarn filaments 13 are knitted together. Yarn filaments 13 are typically made from stretch nylon material, and yarn filaments 14 are typically made from elastomeric polyurethane material, such as SPANDEX material. These yarn filaments 13 and 14 are warp knitted on a circular warp knitting machine, and the material 10 is made to have a cylindrical and tubular shape so that it can be used in a sleeve form.

Warp knitting is defined as the "simultaneous yarn-feeding and loop-forming action occurring at every needle in the needle bar of the machine during the same knitting cycle." *Knitting Technology, 2nd Ed.* by David J. Spencer, Pergamon Press, New York, ©1989, p. 39.

Yarn filaments 13 and 14 are elastic, flexible and resilient so that the sleeve material 10 can be stretched over and snugly retained to a patient's body member. The sleeve material 10 stretches to expand a plurality of spacings 15, which ventilate the body member and leaves portions of the patient's skin exposed to the air. Generally, yarn filaments 13 provide the lengthwise stretch and retention of material 10 while yarn filaments 14 provide the widthsize stretch and retention.

The fabric material is designed and made to have a soft texture so that a patient's body member is easily inserted into the sleeve, and the patient can still fully and easily move the body member therein. The material 10 is also designed and made so that it is not intrusive to the patient's skin or body part.

A prior art invention having characteristics that have just been described above is the elastic tubular sleeve that is widely used as a body cover on injured areas (i.e. a broken bone or wound). Many types of elastic tubular sleeves exist on the market, and they are typically obtained or purchased in the form of a tubular roll. The tubular sleeve can be cut to a certain length so that the injured body member can be inserted into the sleeve, and the cast or bandage is then placed over the sleeve. The sleeve prevents the cast or bandage from sticking to the injured body member. These sleeves can also be made from stretch nylon and elastomeric polyurethane (i.e. SPANDEX material) material. These sleeves are typically warp knitted together on a circular warp knitting machine, and the material has a cylindrical and tubular shape so that it can be used in sleeve form.

Therefore, these elastic tubular sleeves can be used and adapted as sleeve material 10 for protectively stabilizing and securing an intravenous device to a patient's body member. The specifications of a particular elastic tubular sleeve that adapts well for the purposes of stabilizing and securing an intravenous device will be given later.

Sleeve material 10 can be adapted and used in a number of embodiments in which various body members such as a patient's hands, arms or legs are inserted into the sleeve material 10. Two embodiments in which a patient's hands is inserted into the sleeve material 10 are now described in more detail.

The First Embodiment

As seen in FIG. 2, sleeve 20, which is the first embodiment and preferred mode of the invention for protectively stabilizing and securing an intravenous device, is made from sleeve material 10. Sleeve material 10 is adapted so that a patient's hand 50 can insert through it by making a hole 21 near the first end 11 of the material 10. The patient's hand 50 is inserted through the second end 12 of the sleeve material 10, and the sleeve 20 is stretched over the patient's hand 50. The patient's thumb 51 is inserted through hole 21, and the patient's other four fingers 52 are all inserted through the first open end 11. Sleeve 20 generally encircles the backside and palm side of the patient's hand 50.

When a patient's hand 50 is inserted through sleeve 20, yarn filaments 13 generally stretch over and retain to the patient's hand 50 in a lengthwise direction, and yarn filaments 14 generally stretch over and retain to the patient's hand 50 in a widthsize direction. A plurality of spacings 15 located within the sleeve 20 are thereby enlarged when the sleeve 20 is stretched over the patient's hand 50.

FIG. 2A is an enlarged view of a portion of FIG. 2 showing the intravenous device 40 attached to the patient's hand 50 and stabilized and secured by sleeve 20. Intravenous device 40 comprises an intravenous container 43, a needle 41, and a tube 42 that connects the container 43 to needle 41. The intravenous device 40 is secured by first inserting the needle 41 into the patient's hand 50 and then stretching the sleeve 20 over the needle 41 and portions of the tube 42 when the patient's hand 50 is inserted into sleeve 20. As shown in FIG. 2A, sleeve 20 covers the portions of the intravenous device 40 that are to be secured to the patient's hand 50.

Alternatively, the intravenous device 40 can be secured by first stretching sleeve 20 over the patient's hand 50 and then inserting needle 41 through at least one spacing 15 into the patient's hand 50 (i.e. as shown in FIG. 3). The needle 41 is inserted through a spacing 15 and underneath several yarn filaments 13 or 14. The yarn filaments 13 or 14 elastically retain the needle 41 to the patient's hand 50. Needle 41 can be placed under any number of yarn filaments 13 or 14, and even a portion of tube 42 can even be retained to the patient's hand 50 by inserting it through a spacing 15 and underneath any number of yarn filaments 13 or 14 as well.

The Second Embodiment

Figure 4:
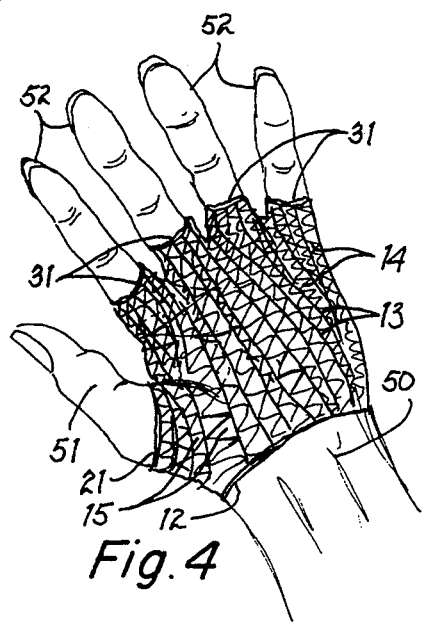
FIG. 4—Perspective view of a second embodiment of a tubular sleeve stabilizing and securing an intravenous device to a patient's hand showing the palm side of the hand.

As shown in FIGS. 3 and 4, sleeve 30, which is the second embodiment for protectively stabilizing and securing an intravenous device, is also made from sleeve material 10. The sleeve material 10 is adapted so that a patient's hand 50 can be inserted through it by making hole 21 as well as making four other holes 31 near the first end 11 of the material 10. The patient's hand 50 is inserted through the second end 12 of the sleeve material 10, and the sleeve 20 is stretched over the patient's hand 50. The patient's thumb 51 is inserted through hole 21 and each of the patient's other four fingers 52 is inserted through one of the holes 31.

Sleeve 30 as shown in FIGS. 3 and 4 retains intravenous device 40, needle 41, and tube 42 in the same manner as was discussed earlier for sleeve 20 (i.e. one example is shown in FIG. 2A). The intravenous device 40 may be protectively retained to the patient's hand 50 by securing the needle 41 and portions of the tube 42 underneath sleeve 20 which elastically retains intravenous device 40 to the patient's hand 50 as shown in FIG. 2A, or alternatively, the intravenous device 40 may be protectively retained to the patient's hand 50 by securing needle 41 underneath sleeve 20 as shown in FIG. 3.

Specifications Of An Elastic Tubular Sleeve Used in a Working Example

As stated earlier, elastic tubular sleeves can be used as the sleeve material 10 in making the present invention for protectively stabilizing and securing an intravenous device to a patient's hand. The following specifications are for an elastic tubular sleeve that is easily and well adapted as a working example for various embodiments of the present invention:

1. Name: X-SPAN TM elastic tubular sleeve.
2. Manufacturer: ALBA Health Products, Co., Valdese, N.C.
3. Various circumference sizes: 1"–10".
4. Lengthwise material: Stretch Nylon Yarn.
   Specifications of Stretch Nylon Yarn:
   a. Two (2) ply.
   b. Seventy (70) vinier.
   c. Thirty-four (34) filaments in each of the two strands of yarn.
   Widthsize material: Elastomeric Polyurethane Yarn (i.e. SPANDEX TM or GLOBE SPAN TM yarn).
   Specifications of Elastomeric Polyurethane Yarn:
   a. Single filament.
   b. One hundred eighty-four (184) vinier.
6. Double cover for the material.
   a. Thirty (30) vinier yarn.
   b. Ten (10) filaments for each cover.
7. Knit type: Warp Type Knitting.
8. Knitting machine type: Circular Type Machine
   Specifications of machine:
   a. Thirty (30) needle machine used to make 1", 2", or 3" circumference by varying the tension of the machine.
   b. Eighty-four (84) needle machine used to make 4", 5", or 6" circumference material by varying the tension of the machine.

The foregoing description of a preferred embodiment and best mode of the invention known to applicant at the time of filing the application has been presented for the purposes of illustration and description. It is not intended to be exhaustive or to limit the invention to the precise form disclosed, and obviously many modifications and variations are possible in the light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed:

1. A method for protectively stabilizing and securing an intravenous device to a body member of a patient, comprising the steps of:
   providing a tubular sleeve made of stretchable fabric encompassing a plurality of tiny spacings and having two open ends;
   attaching the intravenous device to the body member;
   simultaneously stretching the sleeve fabric while inserting the body member through the sleeve so that the sleeve encircles and is elastically retained on the body member;
   enlarging the spacings in the sleeve when the sleeve is stretched over the body member; and securing the intravenous device between the sleeve fabric and the body member.

2. The method for protectively stabilizing and securing an intravenous device according to claim 1 wherein the inserting step further comprises the step of:
inserting a hand through the tubular sleeve so that the sleeve encircles and is elastically retained on the hand therein.

3. The method for protectively stabilizing and securing an intravenous device according to claim 2 further comprising the steps of:
providing at least one hole proximate an end of the sleeve; and
inserting a finger of the hand through each hole.

4. The method for protectively stabilizing and securing an intravenous device according to claim 1 wherein the step of providing a tubular sleeve made of stretchable fabric comprises the steps of:
extending a plurality of stretch nylon yarn filaments adjacent to each other vertically from one end of the fabric to the other end;
knitting a plurality of elastomeric polyurethane yarn filaments between each of the vertical stretch nylon yarn filaments so that the stretch nylon yarn filaments are knitted together; and
circularly warp knitting the stretch nylon yarn and the elastomeric polyurethane yarn filaments together so that a cylindrical, tubular fabric is formed to make up the sleeve.

5. The method for protectively stabilizing and securing an intravenous device according to claim 4 wherein the step of inserting a body member through the sleeve is achieved by:
stretching the stretch nylon yarn filaments and the elastomeric polyurethane yarn filaments over the body member to elastically retain the sleeve on the body member.

6. The method for protectively stabilizing and securing an intravenous device according to claim 5 wherein the step of enlarging the spacings in the sleeve further comprises the step of:
enlarging the spacings between the stretch nylon yarn filaments and the elastomeric polyurethane yarn filaments when the yarn filaments are stretched over the body member.

7. The method for protectively stabilizing and securing an intravenous device according to claim 1 wherein the step of providing a tubular sleeve made of stretchable fabric further comprises the step of:
providing a stretchable fabric that is an elastic, soft, resilient material enabling the body member to be easily inserted through the tubular sleeve while allowing the body member to be fully and easily moveable therein.

8. The method for protectively stabilizing and securing an intravenous device according to claim 1 wherein the step of securing the intravenous device between the sleeve fabric and the body member further comprises the step of:
stretching the sleeve fabric over the intravenous device which is attached to the body member so that the intravenous device is elastically retained to the body member.

9. The method for protectively stabilizing and securing an intravenous device according to claim 8 wherein the step of securing the intravenous device between the sleeve fabric and the body member further comprises the step of:
stretching the sleeve fabric over a needle and a tube portion of the intravenous device which is attached to the body member so that the intravenous device is elastically retained and further secured to the body member.

10. The method for protectively stabilizing and securing an intravenous device according to claim 1 wherein the step of enlarging the spacings further comprises the step of:
ventilating the body member when the sleeve is stretched over and elastically retained on the body member.

11. An apparatus for protectively stabilizing and securing an intravenous device to a body member of a patient, comprising:
a tubular sleeve made of a stretchable fabric forming a loose knit wall structure adapted to encircle the body member and be elastically retained thereon, and having
a central opening for inserting the body member therethrough,
at least one additional body member opening in the wall structure through which a portion of the body member may also be inserted for stably positioning the sleeve on the body member, and
a plurality of tiny spacings in the wall structure for ventilating the body member when superimposed thereover,
whereby an intravenous device when inserted in the vein of a body member may be comfortably and securely retained in position between the body member and overlying sleeve fabric.

* * * * *